US005499977A

United States Patent [19]
Marx

[11] Patent Number: 5,499,977
[45] Date of Patent: Mar. 19, 1996

[54] MALE EXTERNAL CATHETER WITH VACUUM ASSIST

[76] Inventor: Sherwood D. Marx, 6478 S. M St., Tacoma, Wash. 98408

[21] Appl. No.: 335,891

[22] Filed: Nov. 8, 1994

[51] Int. Cl.⁶ ........................................ A61F 5/44
[52] U.S. Cl. ............................... 604/352; 604/349
[58] Field of Search ........................ 604/349–352; 128/842, 843, 844

[56] References Cited

U.S. PATENT DOCUMENTS

| | | | |
|---|---|---|---|
| 3,421,504 | 1/1969 | Gibbons | 604/349 |
| 3,421,507 | 1/1969 | Gresham | 604/349 |
| 3,820,553 | 6/1974 | Jones | 604/349 |
| 4,713,067 | 12/1987 | Rothenberg et al. | 604/350 |

Primary Examiner—Randall L. Green
Assistant Examiner—Mark O. Polutta

[57] ABSTRACT

A new and improved male external catheter with vacuum assist for providing a device that can be incorporated onto any male patient without worry of leaking or discomfort. The device having a catheter with a rolled up ring thereattached for securement around a male's organ and an elongated hollow extension thereattached. The elongated hollow extension has a plurality of annular grooves thereon. A plastic tube removably receives the catheter therein. The rolled up ring of the catheter optionally rolls atop the plastic for application to a user. A rubber bulb is secured to the plastic tube. The rubber bulb functions as a vacuum for the user.

1 Claim, 4 Drawing Sheets

MALE EXTERNAL CATHETER WITH VACUUM ASSIST

BACKGROUND OF THE INVENTION

1. Field of the Invention

The present invention relates to a male external catheter with vacuum assist and more particularly pertains to providing a device that can be incorporated onto any male patient without worry of leaking or discomfort with a male external catheter with vacuum assist.

2. Description of the Prior Art

The use of catheters is known in the prior art. More specifically, catheters heretofore devised and utilized for the purpose of receiving urinary fluids are known to consist basically of familiar, expected and obvious structural configurations, notwithstanding the myriad of designs encompassed by the crowded prior art which have been developed for the fulfillment of countless objectives and requirements.

By way of example, U.S. Pat. No. 5,211,640 to Wendler discloses a male urinary incontinence device.

U.S. Pat. No. 5,013,308 to Sullivan et al. discloses an external male catheter.

U.S. Pat. No. 4,589,874 to Riedel et al. discloses an external male catheter and applicator collar therefor.

U.S. Pat. No. 5,059,190 to Novak discloses an external male urinary catheter and method and apparatus for manufacturing such a catheter.

U.S. Pat. No. 4,997,427 to Bowen discloses an external male urinary catheter.

While these devices fulfill their respective, particular objective and requirements, the aforementioned patents do not describe a male external catheter with vacuum assist for providing a device that can be incorporated onto any male patient without worry of leaking or discomfort.

In this respect, the male external catheter with vacuum assist according to the present invention substantially departs from the conventional concepts and designs of the prior art, and in doing so provides an apparatus primarily developed for the purpose of providing a device that can be incorporated onto any male patient without worry of leaking or discomfort.

Therefore, it can be appreciated that there exists a continuing need for a new and improved male external catheter with vacuum assist which can be used for providing a device that can be incorporated onto any male patient without worry of leaking or discomfort. In this regard, the present invention substantially fulfills this need.

SUMMARY OF THE INVENTION

In the view of the foregoing disadvantages inherent in the known types of catheters now present in the prior art, the present invention provides an improved male external catheter with vacuum assist. As such, the general purpose of the present invention, which will be described subsequently in greater detail, is to provide a new and improved male external catheter with vacuum assist and method which has all the advantages of the prior art and none of the disadvantages.

To attain this, the present invention essentially comprises a catheter having an open first end, an open second end, and an intermediate extent therebetween. The open first end has a rolled up ring thereattached for securement around a male's organ. The second end has an elongated hollow extension thereattached. The elongated hollow extension has a plurality of annular grooves thereon. The angular grooves are adapted for coupling with a plastic tube that is secured to a bag or container for disposing of a male's urine. The intermediate extent is constructed of a soft latex for ease of application and comfort. The device contains a plastic tube having an open first end, an open second end, and an intermediate extent therebetween. The open first end has an opening twice that of the open second end. The open first end removably receives the catheter therein. The rolled up ring of the first end of the catheter optionally rolls atop the open first end for application to a user. The open second end has a securement means thereattached. The device contains a rubber bulb having an open first end, a closed rounded second end, and a hollow interior. The open first end is secured to the securement means of the open second end of the plastic tube. The rubber bulb functions as a vacuum for the user.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved male external catheter with vacuum assist which has all the advantages of the prior art catheters and none of the disadvantages.

It is another object of the present invention to provide a new and improved male external catheter with vacuum assist which may be easily and efficiently manufactured and marketed.

It is a further object of the present invention to provide a new and improved male external catheter with vacuum assist which is of durable and reliable construction.

An even further object of the present invention is to provide a new and improved male external catheter with vacuum assist which is susceptible of a low cost of manufacture with regard to both materials and labor, and which accordingly is then susceptible of low prices of sale to the consuming public, thereby making such a male external catheter with vacuum assist economically available to the buying public.

Still yet another object of the present invention is to provide a new and improved male external catheter with vacuum assist which provides in the apparatuses and methods of the prior art some of the advantages thereof, while simultaneously overcoming some of the disadvantages normally associated therewith.

Even still another object of the present invention is to provide a new and improved male external catheter with vacuum assist for providing a device that can be incorporated onto any male patient without worry of leaking or discomfort.

Lastly, it is an object of the present invention to provide a new and improved male external catheter with vacuum assist with a catheter having a rolled up ring thereattached for securement around a male's organ and an elongated hollow extension thereattached. The elongated hollow extension has a plurality of annular grooves thereon. A plastic tube removably receives the catheter therein. The rolled up ring of the catheter optionally rolls atop the plastic for application to a user. A rubber bulb is secured to the plastic tube. The rubber bulb functions as a vacuum for the user.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various Figures.

DESCRIPTION OF THE PREFERRED EMBODIMENT

Figure 1:
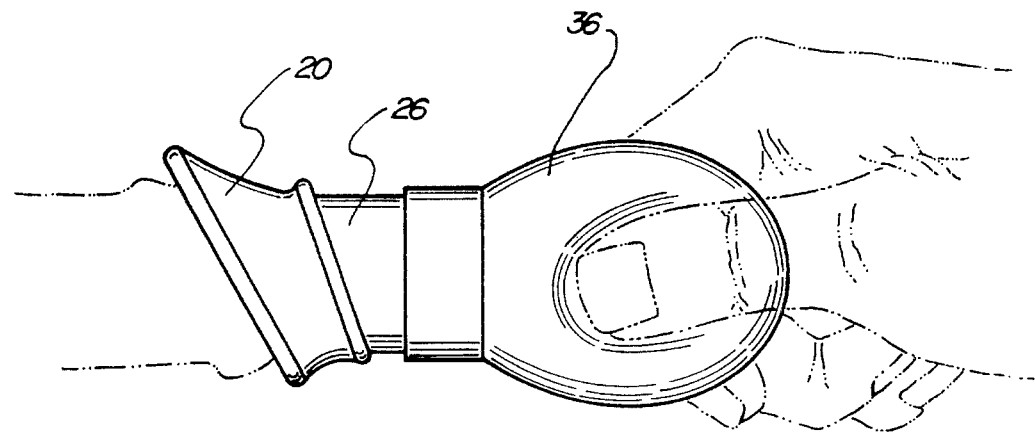
FIG. 1 is a side view of the preferred embodiment of the male external catheter with vacuum assist constructed in accordance with the principles of the present invention.
Figure 2:
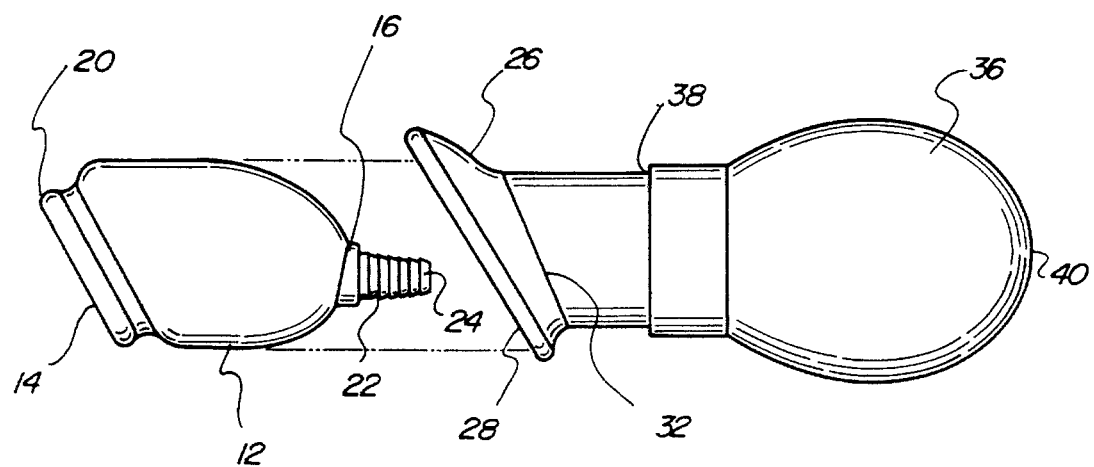
FIG. 2 is a side view of the present invention illustrating the catheter removed from the plastic tube and the rubber bulb.
Figure 3:
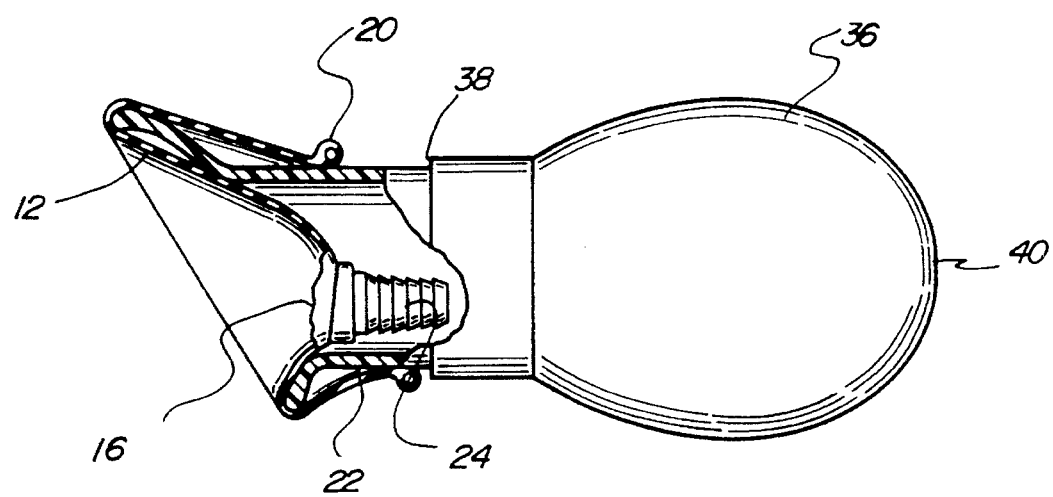
FIG. 3 is a is a cross-sectional side view of the catheter within the plastic tube.
Figure 4:
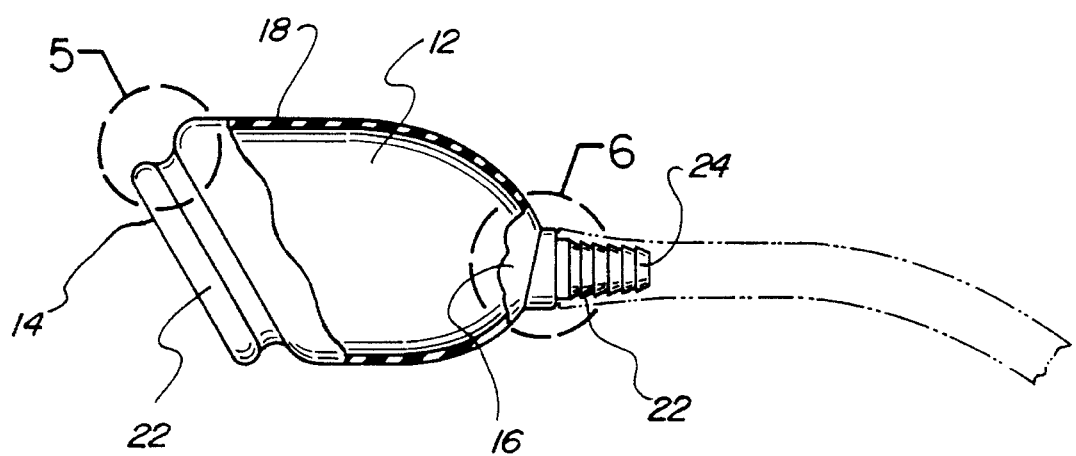
FIG. 4 is a side view of the catheter and its optional coupling with a container tube.
Figure 5:
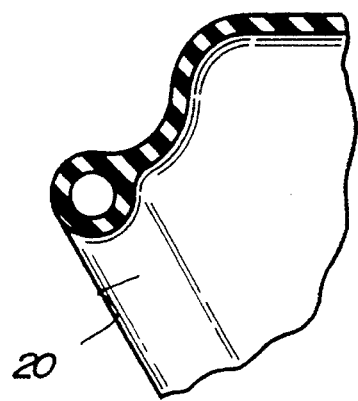
FIG. 5 is a cross-sectional view of the rolled ring of the catheter as seen from FIG. 4.
Figure 6:
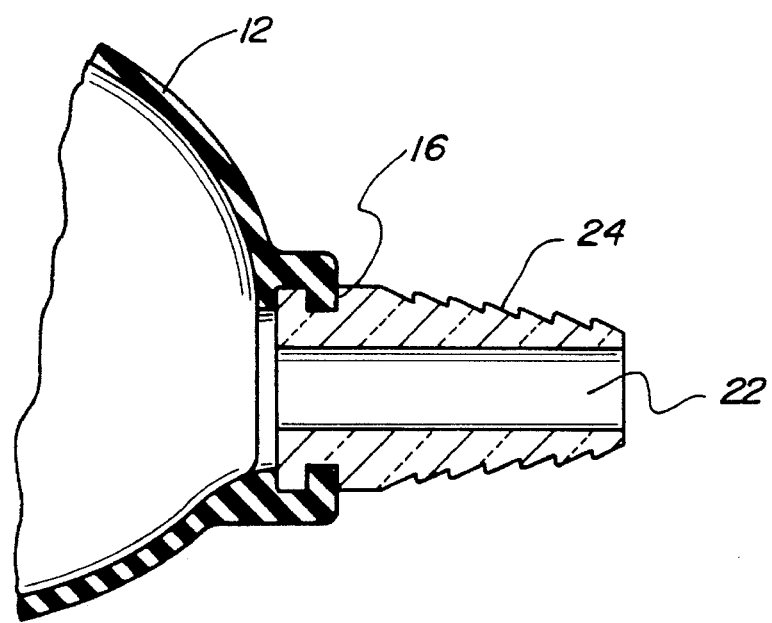
FIG. 6 is a cross-sectional view of the annular end portion of the catheter as seen from FIG. 4.
Figure 7:
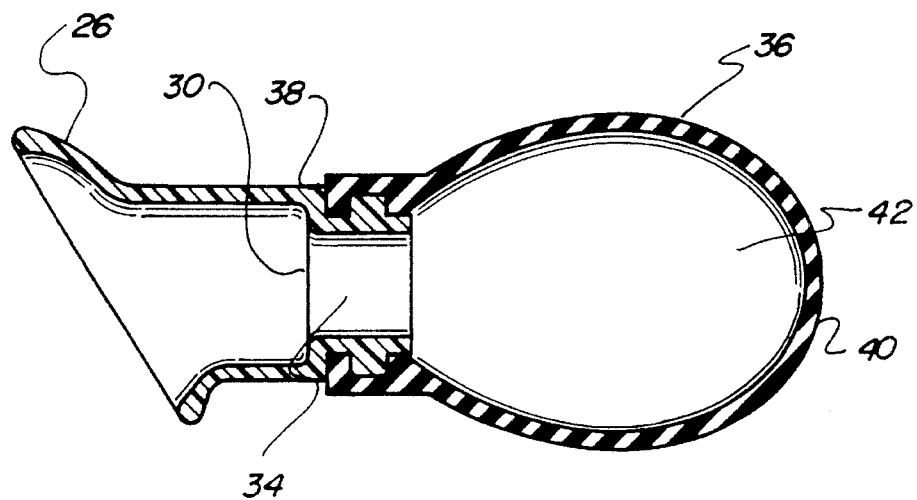
FIG. 7 is a cross-sectional view of the plastic tube and the rubber bulb and their coupling.
Figure 8:
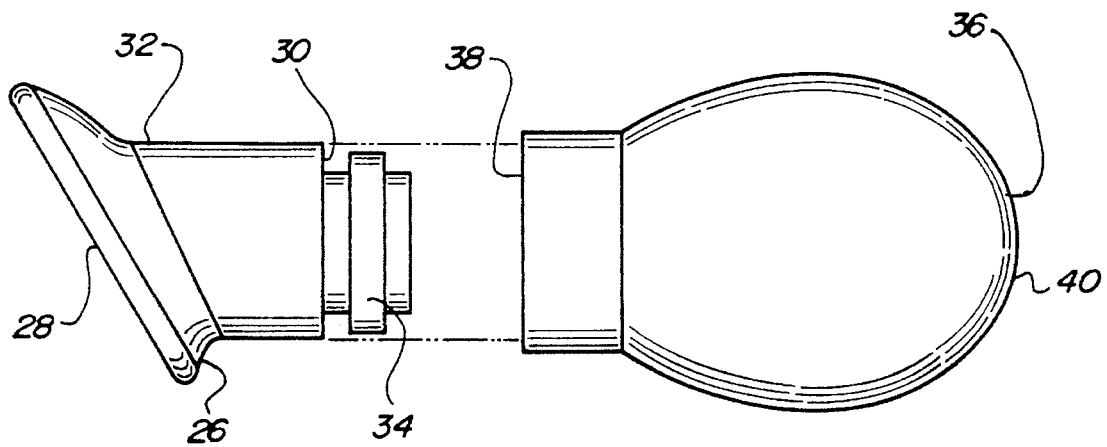
FIG. 8 is a side view of the plastic tube and the rubber bulb illustrating disassembly.

With reference now to the drawings, and in particular, to FIG. 1 thereof, the preferred embodiment of the new and improved male external catheter with vacuum assist embodying the principles and concepts of the present invention and generally designated by the reference number 10 will be described.

Specifically, it will be noted in the various Figures that the device relates to a new and improved male external catheter with vacuum assist for providing a device that can be incorporated onto any male patient without worry of leaking or discomfort. In its broadest context, the device consists of a catheter, a plastic tube, and a rubber bulb.

The device 10 contains a catheter 12 having an open first end 14, an open second end 16, and an intermediate extent 18 therebetween. The open first end 14 has a rolled up ring 20 thereattached for securement around a male's organ. The open first end 14 and the rolled up ring 20 are constructed of a light weight material, such as latex, similar to a condom so that the open first end 14 and the rolled up ring 20 will collapse around the male's organ and provide a seal that will prevent any moisture or urine from leaking out when in place around the organ. The second 16 has an elongated hollow extension 22 thereattached. The elongated hollow extension 22 has a plurality of annular grooves 24 thereon. The annular grooves 24 are adapted for coupling with a plastic tubing that is secured to a bag or container for disposing of a male's urine. The elongated hollow extension 22 is constructed of a rigid plastic material that can withstand the pressure of securement to the plastic tubing. The intermediate extent 18 is constructed of a soft latex for ease of application and comfort.

The device 10 contains a plastic tube 26 having an open first end 28, an open second end 30, and an intermediate extent therebetween 32. The open first end 28 has an opening twice that of the open second end 30. The open first end 28 removably receives the catheter 12 therein. The rolled up ring 20 of the first end 14 of the catheter 12 optionally rolls atop the open first end 28 for application to a user. When the user decides to secure the catheter around their organ, the rolled up ring 20 is rolled up over the a lip formed by the open first end 28. The entire catheter 12 is within the plastic tube 26 with the exception of the rolled up ring 20. The open first end 28 is then ready to receive the male's organ. The open second end 30 has a securement means 34 thereattached. The securement means is preferably an extension that allows an attachment to easily be secured to it and easily removed from it generally to allow the plastic tube 26 to be thoroughly cleaned.

The device 10 contains a rubber bulb 36 having an open first end 38, a closed rounded second end 40, and a hollow interior 42. The open first end 38 is secured to the securement means 34 of the open second end 30 of the plastic tube 26. The rubber bulb 36 functions as a vacuum for the user. The rubber bulb 36 is simply squeezed, placed on the head of the organ and released. The vacuum created from this action pulls the organ into the catheter, into position for ring 20. The rolled up ring 20 is then rolled off of the plastic tube to fit over the organ. By doing this, the plastic tube 26 and the rubber bulb 36 are removed and the plastic tubing is secured to the annular grooves 24 of the elongated hollow extension 22 of the catheter 12 and the user is ready to exercise any task desired.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by LETTERS PATENT of the United States is as follows:

1. A new and improved male external catheter with vacuum assist for providing a device that can be incorporated onto any male patient without worry of leaking or discomfort comprising, in combination:

a catheter having an open first end, an open second end, and an intermediate extent therebetween, the open first end having a rolled up ring thereattached for securement around a male's organ, the second end having an elongated hollow extension thereattached, the elongated hollow extension having a plurality of annular grooves thereon, the angular grooves adapted for coupling with a plastic tube that is secured to a bag or container for disposing of a male's urine, the intermediate extent constructed of a soft latex for ease of application and comfort;

a plastic tube having an open first end, an open second end, and an intermediate extent therebetween, the open first end having an opening twice that of the open second end, the open first end removably receiving the catheter therein, the rolled up ring of the first end of the catheter optionally rolls atop the open first end for application to a user, the open second end having a securement means thereattached; and a rubber bulb having an open first end, a closed rounded second end, and a hollow interior, the open first end secured to the securement means of the open second end of the plastic tube, the rubber bulb functioning as a vacuum for the user.

* * * * *